(12) United States Patent
Kilgard et al.

(10) Patent No.: US 7,024,398 B2
(45) Date of Patent: Apr. 4, 2006

(54) COMPUTER-IMPLEMENTED METHODS AND APPARATUS FOR ALLEVIATING ABNORMAL BEHAVIORS

(75) Inventors: Michael Kilgard, Richardson, TX (US); Michael M. Merzenich, San Francisco, CA (US); Shaowen Bao, San Francisco, CA (US)

(73) Assignees: Scientific Learning Corporation, Berkeley, CA (US); The University of Texas, Austin, TX (US); The Regents of the University of California, Oakland, CA (US)

( * ) Notice: Subject to any disclaimer, the term of this patent is extended or adjusted under 35 U.S.C. 154(b) by 625 days.

(21) Appl. No.: 10/000,844

(22) Filed: Nov. 1, 2001

(65) Prior Publication Data

US 2002/0116352 A1    Aug. 22, 2002

Related U.S. Application Data

(60) Provisional application No. 60/245,652, filed on Nov. 2, 2000.

(51) Int. Cl.
G06F 15/18    (2006.01)

(52) U.S. Cl. ...................................................... 706/25

(58) Field of Classification Search .................. 706/25, 706/10; 434/236
See application file for complete search history.

(56) References Cited

U.S. PATENT DOCUMENTS

| | | | | |
|---|---|---|---|---|
| 4,692,147 A | * | 9/1987 | Duggan | 604/891.1 |
| 5,377,258 A | | 12/1994 | Bro | 379/93 |
| 5,678,571 A | | 10/1997 | Brown | 128/898 |
| 5,711,316 A | * | 1/1998 | Elsberry et al. | 128/898 |
| 5,722,418 A | | 3/1998 | Bro | 128/732 |
| 5,725,472 A | | 3/1998 | Weathers | |
| 5,910,107 A | | 6/1999 | Iliff | 600/300 |
| 5,911,581 A | | 6/1999 | Reynolds et al. | 434/236 |

(Continued)

FOREIGN PATENT DOCUMENTS

WO    WO 93/02622    2/1993

(Continued)

OTHER PUBLICATIONS

Ahissar, Merav & Shaul Hochstein, "Task Difficulty and the Specificity of Perceptal Learning", Nature, vol. 387, May 22, 1997.

(Continued)

*Primary Examiner*—Anthony Knight
*Assistant Examiner*—Michael B. Holmes
(74) *Attorney, Agent, or Firm*—Beyer Weaver & Thomas, LLP (57) ABSTRACT

The invention described herein provides computer-implemented methods and systems for alleviating an abnormal behavior, such as a behavior associated with a fear, abnormal activity, or obsession. It has been found that behaviorally abnormal self-sustaining behaviors may be unlearned or diminished through directed forms of computer-implemented interaction. The computer-implemented interaction is generally directed to reduce the neurological representations of inputs and actions associated with the abnormal behavior. The interaction will typically comprise strategically and repeatedly presenting computer-implemented stimuli including context related to the abnormal behavior. The computer-implemented stimuli are then repeatedly presented and altered over time in a manner that alleviates the abnormal behavior. For example, the content of the computer-implemented stimuli may change to gradually vary in their ability to trigger an episode in the person. In this manner, the neurological representation pertaining to the undesirable behavior may be gradually reduced.

21 Claims, 5 Drawing Sheets

U.S. PATENT DOCUMENTS

| | | | |
|---|---|---|---|
| 5,913,310 A | 6/1999 | Brown | 128/897 |
| 5,940,801 A | 8/1999 | Brown | |
| 6,019,607 A | 2/2000 | Jenkins et al. | 434/116 |
| 6,030,226 A | 2/2000 | Hersh | |
| 6,053,739 A | 4/2000 | Stewert et al. | |
| 6,165,126 A | 12/2000 | Merzenich et al. | 600/300 |
| 6,231,344 B1* | 5/2001 | Merzenich et al. | 434/236 |
| 6,351,675 B1* | 2/2002 | Tholen et al. | 607/59 |

FOREIGN PATENT DOCUMENTS

| | | |
|---|---|---|
| WO | WO 94/04072 | 3/1994 |
| WO | WO 94/06088 | 3/1994 |
| WO | WO 95/29447 | 11/1995 |
| WO | WO 97/06730 | 2/1997 |
| WO | WO 97/34526 | 9/1997 |

OTHER PUBLICATIONS

Bakin, Jonathan S. and Norman M. Weinberger, "Induction of a Physiological Memory in the Cerebral Cortex by Stimulation of the Nucleus Basalis".

Bjordahl, Terrance S., "Induction of Long-Term Receptive Field Plasticity in the Auditory Cortex of the Walking Guinea Pig by Stimulation of the Nucleus Basalis", Behavioral Neuroscience, 1998, vol. 112., No. 3, 467-479, Copyright 1998 by the American Psychological Associates, Inc.

Buonomano, Dean V. and Michael M. Merzenich, "Cortical Plasticity: From Synapses to Maps" Annu. Rev. Neurosci, 1998, 21: 49-86, Copyright 1998 by Annual Reviews Inc.

J.-M.Edeline, B. Hars, C. Maho, E.Hennevin, "Transient and prolonged facilitation of tone evoked responses induced by basal forebrain stimulations in the rat auditory cortex", Experimental Brain Research, Springer-Verlag 1994.

J.-M. Edeline, C. Maho, B. Hars, E. Hennevin, "Non-awakening basal forebrain stimulation enhances auditory cortex responsiveness during slow-wave sleep".

Elbert, Thomas, Christo Pantev, Christian Wienbruch, Brigitte Rockstroh, Edward Taub, "Increased Cortical Representation of the Fingers of the Left Hand in String Players", Science, vol. 270 Oct. 13, 1995.

Esser, Karl-Heinz, Curtis J. Condon, Nobuo Suga, Jagmeet S. Kanwal, "Syntax Processing by auditory cortical neurons in the FM-FM area of the mustached bat *Pteronotus parnellii*", Proc. Natl. Acad. Sci, USA vol. 94, pp. 14019-14024, Dec. 1997 Neurobiology.

Friston, Karl J. "The Disconnection Hypothesis", 1998 Elsevier Science B.V.

Fyer, Abby J. "Current Approaches to Etiology and Pathophysiology of Specific Phobia", 1998 Society of Biological Psychiatry.

Glanzman, David L. "The cellular basis of classical conditioning in *Aplysia californica*-it's less simple than you think", 1995, Elsevier Science ltd., TINS vol. 18 No. 1.

B. Hars, C. Maho J.-M. Edeline and E. Hennevin, Basal Forebrain Stimulation Facilitates Tone-Evoked Responses in the Auditory Cortex of Awake Rat.

Hasselmo, Michael E. "Neuromodulation and cortical function modeling the Physiological basis of behavior",1995 Elsevier Science B.V.

Howard, Matthew A., III., Daniel J. Simons, "Physiologic efforts of nucleus basalis magnocellularis stimulation on rat barrel cortex neurons", Exp. Brain Res (1994)102;21-33.

Jenkins, William M., Michael M. Merzenich, Marlene T. Ochs, Terry Allar, Eliana Guic-Robles, "Functional Reorganization of Primary Somatosensory Cortex in Adult Owl Monkeys After Behaviorally Controlled Tactile Stimulation", 1990 The American Physiological Society.

Juliano, Sharon L., Wu Ma, and Don Eslin, "Cholinergic depletion prevents expansion of topographic maps in somatosensory cortex", Proc. Natl. Acad Sci, USA vol. 88, pp. 780-784, Feb. 1991.

Kilgard, Michael P. and Michael M. Merzenich, "Distributed Representation of spectral and temporal information in rat primary auditory cortex" Hearing Research 134 (1999) 16-28.

Kilgard, Michael P and Michael M. Merzenich, "Cortical Map Reorganization Enabled by Nucleus Basalis Activity", Science,vol. 279,Mar. 13, 1998.

Kilgard, Michael P. and Michael M. Merzenich, "Plasticity of temporal information processing in the primary auditory cortex", nature neuroscience,vol. 1 No. 8, Dec. 1998.

Kilgard, Michael P., Pritesh K. Pandya, Jessica Vasquez, Anil Gehi, Christoph E. Schreiner and Michael M. Merzenich, Sensory Input Directs Spatial and Temporal Plasticity in Primary Auditory Cortex, 2001 The American Physiological Society.

McGaughy, J., B.J. Everitt, T.W. Robbins, M. Sarter, The role of cortical cholinergic afferent projections in cognition: impact of new selective immunotoxins, 2000 Elsevier Science B.V.

Merzenich, M. B. Wright, W. Jenkins, C. Xerri, N. Byl, "Cortical Plasticity Underlying Perceptual, Motor, and Cognitive Skill Development: Implications for Neurorehabilitation".

Merzenich, Michael M., William Jenkins, Paul Johnston, Christoph Schreiner, Steven L. Miller, Paula Tallal, "Temporal Processing Deficits of Language-Learning Impaired Children Ameliorated by Training" Science vol. 271, Jan. 5, 1996.

Merzenich, M. M., G.H. Recanzone, W.M. Jenkins and K.A.Grajski, Adaptive Mechanisms in Cortical Networks Underlying Cortical Contributions to Learning and Nondeclarative Memory, 1990 Cold Spring Harbor Laboratory Press.

Muhlnickel, Werner, Thomas Elbert, Edward Taub, and Herta Flor, "Reorganization of auditory cortex in tinnitus" Proc. Natl. Acad. Sci. USA, vol. 95, pp, 10340-10343, Aug. 1998 Psychology.

Recanzone, Gregg H., Michael M. Merzenich, William M. Jenkins, Kamil A. Grajski and Hubert R. Dinse, "Topographic Reorganization of the Hand Representation in Cortical Area 3b of Owl Monkeys Trained in Frequency-Discrimination Task", Journal of Neurophsiology, vol. 67, No. 5, May 1992.

Recanzone, G.H., C.E. Schreiner, and M. M. Merzenich, "Plasticity in the Frequency Representation of Primary Auditory Cortex following Discrimination Training in Adult Owl Monkeys", The Journal of Neuroscience, Jan. 1993.

Sterr, A., Muller, M.M., Elbert, T., Rockstroh, B., Pantev, C. and Taub, E. Changed perceptions in Braille readers. Nature 391, 134-5 (1998).

Tallal, Paula, Steve L. Miller, Gail Bedi, Gary Byma, Xiaoquin Wang, Srikantan S. Nagarajan, Christoph Schriener, William M. Jenkins, Michael M. Merzenich., "Language Comprehension in Language-Learning Impaired Children Improved with Acoustically Modified Speech", Science, vol. 271, Jan. 5, 1996.

Tremblay, Nicole, Richard A. Warren, and Robert W. Dykes, "Electrophysiological Studies of Acetylcholine and the Role of the Basal Forebrain in the Somatosensory Cortex of the Cat II Cortical Neurons Excited by Somatic Stimuli", Journal of Neurophysiology.

Wang, Xiaoqin, Michael M. Merzenich, Ralph Beitel, and Christoph E. Schreiner, "Representation of a Species-Specific Vocalization in the Primary Auditory Cortex of the Common Marmoset: Temporal and Spectral Characteristics", Journal of Neurophysiology, vol. 74, No. 6, Dec. 1995.

Webster, Harry H, Uwe-Karsten Hanisch, Robert W. Dykes, and Dietmar Biesold, "Basal Forebrain Lesions with or without Reserpine Injection Inhibit Cortical Reorganization in Rat Hindpaw Primary Somatosensory Cortex Following Sciatic Nerve Section", Sematosensory and Motor Research, vol. 8., No. 4, 1991, pp 327-346, Accepted Sep. 23, 1991.

Webster, H.H., D.D. Rasmusson, R.W. Dykes, R. Schliebs, W. Schober, G. Brukner and D. Biesold, "Long Term Enhancement of Evoked Potentials in Raccoon Somastosensory cortex following co-activation of the nucleus basalis of Meynert Complex and Cutaneous Receptors", Elsevier Science Publishers B.V. (Biomedical Division) 0006-8993, 1991, Brain Research, 545 292-296.

Wolberg, Z. and Newman, J.D., Auditory Cortex of squirrel monkey: response patterns of single cells to species-specific vocalizations, Science,175, 212-4.

Wright, B.A., Lombardino, L.J.,King, W.M., Puranik, C.S., Leonard, C.M. and Merzenich, M.M., Deficits in auditory temporal and spectral resolution in language-impaired children. Nature, 387,176-8 (1997).

Xerri, C., Stern, J.M.and Merzenich, M.M., "Alterations of the cortical representation of the rat ventrum induced by nursing behavior", Jneurosci,14, 1710. (1994).

Bao, Shaowen, Vincent T. Chan, Michael M. Merzenich, "Cortical Remodelling Induced by Activity of Ventral Tegmental Dopamine Neurons", Nature, vol. 412, Jul. 5, 2001.

Byl, N. N., McKenzie, A., and Nagarajan, S.S., "Differences in Somatosensory Hand Organization in a Healthy Flutist and a Flutist with Focal Hand Dystonia", *Journal of Hand Therapy* 302-309, (2000).

Byl, N.N and Melnick, M. "The Neural Consequences of Repetition: Clinical Implications of a Learning Hypothesis", *Journal of Hand Therapy*, 160-174 (1997).

Kilgard, M.P. and Merzenich, M.M., "Order Selective Plasticity in the Primary Auditory Cortex," In *Society for Neuroscience Abstracts* 25:391.

Pepeu, G. and Blandina, P., "The acetycholine, GABA, glutamate triangle in the rat forebrain", *J. Physiology (Paris)* 92,351-355, (1998).

Richardson, R.T. and DeLong, M.R., "Electrophysiological Studies of the Functions of the Nucleus Basalis in Primates", *Adv. Exp. Med. Biol*, 295,233-252. (1991).

Roger Jelliffe, et al., Adaptive control of drug dosage regimens: basic foundations, relevant issues, and clinical examples, International Journal of Bio-Medical Computing 36, (pp. 1-23), © 1994.

Schneider et al. Self-Regulation of Slow Cortical Potentials in Psychiatric Patients: Schizophrenia, © Dec. 1992, Biofeedback and Self-Regulation, vol. 17, No. 4, pp. 277-292.

Tretter F., Perspectives of Computer-Aided Therapy and Rehabilitation in Psychiatry, Jul. 1996, pp. 475-486.

Hermanutz M. and Gestrich J., Computer-assisted Attention Training in Schizophrenics, 1991, European Archives of Psychiatry and Clinical Neuroscience, vol. 240, pp. 282-287.

Frith, C., The role of the prefrontal cortex in self-consciousness: the case of auditory hallucinations, pp. 1505-1512 (1996).

Bruce E. Wexler, M.D., et al., "The Outpatient Treatment of Depression Implications of Outcome Research for Clinical Practice", The Journal of Nervous and Mental Disease, vol. 180, No. 5, May 1992, pp. 277-286.

Ralph H.B. Benedict, et al., "Effects of Attention Training on Information Processing in Schizophrenia", Schizophrenia Bulletin, vol. 20, No. 3, 1994, pp. 537-546.

Patrick W. Corrigan, et al., "Memory and vigilance training to improve social perception in schizophrenia", Schizophrenia Research, © 1995 Elsevier Science B.V., pp. 257-265.

Ian Creese, et al., "Dopamine Receptor Binding Predicts Clinical and Pharmacological Potencies of Antischizophrenic Drugs", © 1976 American Assoc. for the Advancement of Science, Apr. 30, 1976, vol. 192, pp. 481-483.

Ian Creese, et al., "Dopomine Receptors: A Classification", Dept. of Neurosciences, Journal of Clinical Psychopharmacology, © 1982 Williams & Wilkins Co., vol. 2, No. 5, pp. 329-335.

Ricardo Davila, PhD, et al., "Plasma Homovanillic Acid as a Predictor of Response to Neuroleptics", Arch Gen. Psychiatry, vol. 45, Jun. 1988, pp. 564-567.

Ann Delahunty, PhD., et al., "Rehailitation of frontal/executive impairments in schizophrenia", Australian and New Zealand Journal Of Psychiatry, vol. 30, No. 6, Dec. 1996, pp. 760-767.

Andrew J. Saykin, PsyD, et al., "Neuropsychological Function in Schizophrenia-Selective Impairment in Memory and Learning", Arch Gen Psychiatry, vol. 48, Jul. 1991, pp. 618-624.

Colin D. Field et al., "Computer-Aided Cognitive Rehabilitation: Possible Application To The Attentional Deficit Of Schizophrenia, A Report Of Negative Results", © Perceptual and Motor Skills 1997, vol. 85, pp. 995-1002.

Michael F. Green Ph.D., "What Are the Functional Consequences of Neurocognitive Deficits in Schizophrenia?", Am J Psychiatry 153:3, Mar. 1996, pp. 321-330.

M. Hermanutz et al, "Computer-assisted Attention Training in Schizophrenics—A Comparative Study", © Springer-Verlag 1991, European Archives of Psychiatry and clinical Neuroscience 1991, pp. 282-287.

Amy R. Koreen, M.D., et al., "Plasma Homovanillic Acid Levels in First-Episode Schizophrenia—Psychopathology and Treatment Response", Arch Gen Psychiatry, vol. 51, Feb. 1994, pp. 132-138.

Heidi Nisbet et al., "Improving schizophrenic in-patients' Wisconsin card-sorting performance", © 1996 The British Psychological Society, British Journal Of Clinical Psychology (1996) vol. 35, pp. 631-633.

Toshiyuki Sawaguchi et al., "The Role of D1-Dopamine Receptor in Working Memory: Local Injections of Dopamine Antagonists Into the Prefrontal Cortex of Rhesus Monkeys Performing an Oculomotor Delayed-Response Task", Journal of Neurophysiology, Feb. 1994, pp. 515-528.

Andrew J. Saykin, PsyD. et al., "Neuropsychological Deficits in Neuroleptic Naïve Patients with First-episode Schizophrenia", Arch Gen Psychiatry, vol. 51, Feb. 1994, pp. 124-131.

Wolfram Schultz et al., "A Neural Substrate of Prediction and Reward", Science, vol. 275, Mar. 14, 1997, www.sciencemag.org, pp. 1593-1599.

James Seltzer, Ph.D. et al., "Neuropsychological Rehabilitation in the Treatment of Schizophrenia", Connecticut Medicine, Sep. 1997, vol. 61, No. 9, pp. 597-608.

Theodore Van Putten, M.D. et al., "Plasma Homovanillic Acid as a Predictor of response to Fluphenazine Treatment", Psychopharmacology Bulletin, vol. 1, 1989, pp. 89-91.

Masataka Watanabe et al., "Increase of extracellular Dopamine in Primate Prefrontal Cortex During a Working Memory Task", © 1997 The American Physiological Society, pp. 2795-2797.

Bruce E. Wexler et al., "Normal neurocognitive performance after extended practice in patients with schizophrenia", © 1997 Elsevier Science B.V., pp. 173-180.

Graham V. Williams et al., "Modulation of memory fields by dopamine D1 receptors in prefrontal cortex", Nature, vol. 376, Aug. 17, 1995, pp. 572-575.

Daniel S. O'Leary, Ph.D et al., "Auditory Attentional Deficits in Patients with Schizophrenia—A Positron Emission Tomography Study", Arch Gen Psychiatry, vol. 53, Jul. 1996, pp. 633-641.

Dean F. Salisbury et al., "The N2 event-related potential reflects attention deficit in schizophrenia", Elsevier Science B.V., Biological Psychology 39, 1994, pp. 1-13.

Karen Shedlack et al., "Language processing and memory in ill and well siblings from multiplex families affected with schizophrenia", © 1997 Elsevier Science B.V., vol. 25, pp. 43-52.

Stanley V. Catts, M.D. et al., "Brain Potential Evidence for an Auditory Sensory Memory Deficit in Schizophrenia", Am J Psychiatry 152:2; Feb. 1995, pp. 213-219.

U. Schall et al., "A left temporal lobe impairment of auditory information processing in schizophrenia: an event-related potential study", © 1997 Elsevier Science Ireland Ltd., Neuroscience Letters 229, pp. 25-28.

Michael F. Green Ph.D. et al., "Backward Masking Performance in Unaffected Siblings of Schizophrenic Patients—Evidence for a Vulnerability Indicator", Arch Gen Psychiatry, vol. 54, May 1997, pp. 465-472.

Kristin S. Cadenhead et al., "The Relationship of Information-Processing Deficits and Clinical Symptons in Schizotypal Personality Disorder", © 1996 Society of Biological Psychiatry, vol. 40, pp. 853-858.

Sören Nielzéen et al., "Perceptual Grouping due to Pitch and Amplitude in Hallucinating Schizophrenics", Psychopathology 1997, vol. 30, pp. 140-148.

Lynn E. DeLisi et al., "Schizophrenia as a chronic active brain process: a study of progressive brain structural change subsequent to the onset of schizophrenia", © 1997 Elsevier Science Ireland Ltd., Nuroimaging Section 74, pp. 129-140.

Sandra S. Kindermann et al., "Review of functional magnetic resonance imaging in schizophrenia", © 1997 Elsevier Science B.V., Schizophrenia Research 27, pp. 143-156.

Steven M. Silverstein et al., "Reduced Top-Down Influence in Auditory Perceptual Organization in Schizophrenia", Journal of Abnormal Psychology 1996,. vol. 105, No. 4, pp. 663-667.

Nagarajan et al., "Practice-Related Improvements in Somatosensory Interval Discrimination Are Temporally Specific But Generalize Across Skin Location, Hemisphere, and Modality," Feb. 15, 1998, The Journal of Neuroscience, pp. 1559-1570.

* cited by examiner

COMPUTER-IMPLEMENTED METHODS AND APPARATUS FOR ALLEVIATING ABNORMAL BEHAVIORS

CROSS-REFERENCE TO RELATED APPLICATION

This application claims priority under 35 U.S.C. §119(e) from co-pending U.S. Provisional Patent Application No. 60/245,652 filed Nov. 2, 2000, naming Michael M. Merzenich et al. as inventors, and titled "Computer-Implemented Methods and Apparatus for Remediating Abnormal Behaviors", which is incorporated by reference herein for all purposes.

U.S. GOVERNMENT RIGHTS

This application was made in part with government support awarded by the National Institute of Health under grant number NS-10414. The government has certain rights in the invention.

BACKGROUND OF THE INVENTION

The present invention relates to methods and apparatus for alleviating an abnormal behavior. More specifically, the present invention relates to computer-implemented interactive techniques for alleviating a behaviorally abnormal self-sustaining behavior.

Many obsessive or other abnormal behaviors are manifested in a variety of forms, and comprise part of the symptomatology of many neurological and psychiatric impairments and illnesses. For example, the behaviors are often manifested in patients suffering from "obsessive-compulsive disorder" (OCD), a malady affecting more several million Americans. In this syndrome, an individual has an obsessive fear or concern or behavior that arises often, and with weak triggering, or spontaneously, in a manner that is often disruptive to the individual's life. Such an individual may be fearful, for example, of a particular animal, a mode of transportation, particularly social circumstances or settings, possible sources of poisoning, specific or general considerations of health, death, and so forth. The concerns of an OCD patient may be focussed on their health, on some aspect of cleanliness, or related to other personal habits or life circumstances.

Obsessions in another form are expressed by specific fears such as the fear of flying or claustrophobia, in which the obsession involves a highly unlikely, but potentially dangerous, situation. Obsessions in yet another form are expressed in "Traumatic Stress Disorders" (TSDs), in which the obsession involves a disturbing social event that generates ongoing morbid pathology. Obsessions related to the social circumstances, paraphernalia, and other objects and circumstances that predict the likely future availability of or access to addictive drugs can contribute to a craving for them. Obsessions of other classes are manifested in the perseverative behaviors of autistic or other disturbed children, in the often powerfully intruding and self-generating delusions of psychiatric patients, in the grossly abnormal movement behaviors of Parkinsons disease patients, in patients suffering from chronic pain, in patients suffering from incessant, ongoing sounds (tinnitus)—and in innumerable other forms, in neurologically "impaired" and "diseased" patients, as well as in the general human population.

Currently, care for these disorders is primarily limited to low frequency methods such as manual therapy. The manual therapy usually consists of face-to-face interaction in a therapy site such as a physician's office. Therapy frequency is then limited by the convenience or ability of the person to travel to the therapy site. In another costly example, the person may remain in a hospital for high frequency care or assessment of the obsessive or abnormal behavior status. However, the dramatic costs of inpatient health care may make this alternative undesirably expensive. For these reasons, conventional therapy for an obsessive or abnormal behavior is highly limited.

An abnormal behavior may also be expressed as a bad habit that impairs the effective mastery of an important or useful skill or ability. For example, habits developed from earlier behavioral practices may limit and impede the movement, perceptual or cognitive abilities of a child or adult in a manner that limits their successful mastery of important general skills, such as the development of normal mobility, handwriting, or the use of tools, or for example the development of listening skills required to master successful reading or the use of a new language, or for example the development of cognitive skills necessary to develop strong reasoning abilities. In these and in numerous other cases of this kind, the unlearning of bad habits that impede or delay the development of more useful skills can be an important part of successful learning and positive skill development.

Based on the foregoing, it should be evident that there is a need for systems and methods to alleviate obsessive or abnormal behaviors.

SUMMARY OF THE INVENTION

In accordance with one aspect of the present invention, there are provided computerimplemented methods and systems for alleviating an abnormal behavior, such as a behavior associated with a fear, abnormal activity, obsession, or bad habit. It has been found that behaviorally abnormal self-sustaining behaviors may be unlearned or diminished through directed forms of computer-implemented interaction. The computer-implemented interaction is generally directed to reduce the neurological representations of inputs and actions associated with the abnormal behavior. In one embodiment, the interaction is directed to unlearn the behavior. In this embodiment, the interaction will typically comprise strategically and repeatedly presenting computer-implemented stimuli including context related to the abnormal behavior. The computer-implemented stimuli are then altered over time in a manner that alleviates the abnormal behavior. For example, the content of the computer-implemented stimuli may change to gradually vary in their ability to trigger an episode in the person. In this manner, the neurological representation pertaining to the undesirable behavior may be gradually reduced. The computer-implemented interaction is flexibly designed and may be implemented according to the needs of an individual.

In one embodiment, the computer-implemented interaction is designed to provide a person intensely engaging tasks in addition to the stimuli including context related to the abnormal behavior. In another embodiment, the computer-implemented interaction is designed to provide a person stimuli, tasks, and exercises that are configured to expedite neurochemical change in the person, at temporally specific times relative to the stimuli configured to trigger a response related to the abnormal behavior.

In one aspect, the present invention relates to a computer-implemented method for alleviating an abnormal behavior for a human subject. The computer-implemented method employs a computer-based apparatus associated with one or more peripheral devices. The computer-implemented method comprises presenting, using the computer-based apparatus, a computer-implemented stimuli including context related to the abnormal behavior. The computer-implemented method also comprises altering, using the computer-based apparatus, the computer-implemented stimuli including context related to the abnormal behavior, wherein the altering of the stimuli including context facilitates alleviating the abnormal behavior.

In another aspect, the present invention relates to a computer-implemented method for alleviating an abnormal behavior for a human subject. The computer-implemented method employs a computer-based apparatus associated with one or more peripheral devices. The computer-implemented method comprises presenting to the subject, using the computerbased apparatus, one of a set of computer-implemented stimuli, tasks, and exercises that are configured to expedite neurochemical change in the subject. The method also comprises presenting, using the computer-based apparatus, a computer-implemented stimuli including context related to the abnormal behavior. The method further comprises altering, using the computer-based apparatus, the computer-implemented stimuli including context related to the abnormal behavior, wherein the altering of the stimuli including context facilitates alleviating the abnormal behavior.

In yet another aspect, the present invention relates to a computer readable medium including instructions for alleviating an abnormal behavior for a human subject. The instructions employ a computer-based apparatus associated with one or more peripheral devices. The instructions comprise instructions for presenting, using the computer-based apparatus, a computer-implemented stimuli including context related to the abnormal behavior. The instructions also comprise instructions for altering, using the computer-based apparatus, the computer-implemented stimuli including context related to the abnormal behavior, wherein the altering of the stimuli including context facilitates alleviating the abnormal behavior.

In yet another aspect, the present invention relates to a computer-implemented method for delivering computer readable instructions for alleviating an abnormal behavior for a human subject. The instructions employ a computer-based apparatus associated with one or more peripheral devices. The method comprises transmitting, over a signal transmission medium, signals representative of instructions for presenting, using the computer-based apparatus, a computer-implemented stimuli including context related to the abnormal behavior. The method also comprises transmitting, over a signal transmission medium, signals representative of instructions for altering, using the computer-based apparatus, the computer-implemented stimuli including context related to the abnormal behavior, wherein the altering of the stimuli including context facilitates alleviating the abnormal behavior.

These and other features and advantages of the present invention will be described in the following description of the invention and associated Figures.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION OF THE PREFERRED EMBODIMENTS

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In some instances, well known process steps and/or structures have not been described in detail in order to not unnecessarily obscure the present invention.

1. Overview

While not wishing to be bound by theory, the computer-implemented techniques and strategies described herein use observations made by the inventors in studies of the neurological bases of learning.

It has been observed that, in many cases, obsessive and other abnormal behaviorally-self-sustaining sensations, perceptions and behaviors are a product of progressive learning that results in the growth and strengthening of the neurological representations of those sensations, perceptions, and behaviors. Often, this progressive learning occurs on a level at which active neurological representations are unwillingly, uncontrollably and often spontaneously triggered or generated in an individual.

Studies have also shown that reductions in the real extents and the power of the distributed neurological representations of sensory inputs or repetitive actions are often recorded when identical stimuli are repeatedly delivered to a non-attending individual. In one embodiment, this strategy is applied using the computer implemented methods described below for many abnormal behaviors. However, use of this strategy alone may generate a focus of attention to the application of sensory inputs or repetitive actions. For some obsessions, this can result in a strengthening—rather than a weakening—of their neurological representations.

It has further been shown that powerful neurotransmitters influence, and may expedite, the learning process for a person. Dopamine for example, reinforces and strengthens the brain's neurological representations of induced inputs or actions or obsessively reiterated ideation or other dimensions of behavior if it is released shortly after that obsessive stimuli is received. Thus, this timing of dopamine release selectively strengthens changes that underlie the progressive learning and grows the obsession. For the purposes of this invention, a noteworthy second effect is related to dopamine release: dopamine release weakens the representations of inputs or actions or obsessions if it is released shortly before that input or action or obsessive reiteration. The temporal relationship between the dopamine release and the action or obsession varies depending upon the person and the particular action or obsession.

Collectively, these strategies provide numerous computer implemented approaches for weakening the neurological representations of potentially errant or obsessively learned inputs or actions. The two main approaches described herein in detail are:

1) That behaviors are, paradoxically, weakened by repetitive, stereotyped repetition of computer-implemented stimuli delivered in a non-attended context for the human subject. The computer-implemented stimuli typically includes context related to the nature of the behavior, and in some cases, is directed to trigger a response related to the abnormal behavior. As computer interaction progresses, the stimuli changes to weaken the neurological representations related to the abnormal behavior, as will be described in further detail below. This strategy is typically most effective if the presentation of, or triggering of the obsessed activities do not bring the subjects' strong focus on the related obsession stimuli, which may result in their reiterative strengthening by the brain's learning machinery.

2) The behaviors are progressively weakened by providing computer-implemented stimuli or tasks that trigger or otherwise evoke obsessive iterations in a controlled time relationship with the time-controlled release of the neurotransmitters, such as dopamine and acetocholine, that influence, and may expedite, neurochemical change and the learning process for a person.

These approaches are then applied, either alone or together, using a computer implemented approach that is directed to alleviate abnormal behaviors over time. The computer implemented approach employs a computer-based apparatus associated with one or more peripheral devices.

An illustrative example of this invention includes computer-implemented methods for alleviating a fear of flying in a person. In this case, visual stimuli related to the abnormal behavior include pictures of airplanes, airports, cockpits and other images. The computergenerated stimuli may also include sounds relating to flying. The computer-implemented interaction might involve the person in an activity that was intensely demanding and highly rewarding, such as a continually challenging computer game.

According to the first technique, in order to reduce the neurological representation through the repeated presentation of unattended and unrewarded stimuli, a number of disturbing computer-generated stimuli related to the fear, such as one or more images or sounds, might be repeatedly presented. In order to avoid triggering symptoms, the image or sound might initially need to be only peripherally related to the fear, such as a picture of a bird.

According to the second technique, the neurological representation related to the abnormal flying behavior may be reduced by presenting computer-provided stimuli, tasks or games that induce dopamine expression prior to the presentation of the stimulus related to the abnormal behavior. For example, a disturbing image or sound might be presented immediately following a dopamine-inducing reward including in a game. Again, in order to avoid triggering symptoms, the image or sound related to the abnormal behavior might initially need to be only peripherally related to the fear.

In either technique, as computer-implemented interaction progresses and reaction to repeated presentation of the peripherally related stimuli decreases, the stimuli may be altered to more closely resemble the fear; and thus progressively lessen reaction to stimuli related to the abnormal behavior. Thus, as the computer-implemented interaction progresses, neurological representations of the abnormal behavior may be weakened through repetitive presentation of stimuli progressively more related to the abnormal behavior. This eventually permits subsequent presentation and unlearning of stimuli (e.g., airports and eventually planes) that may trigger the activity, fear, or obsession at increasing levels. In one embodiment, the computer-stimuli induced production of neurotransmitters, such as dopamine, may expedite the neurochemical change mechanisms and progression.

Figure 1:
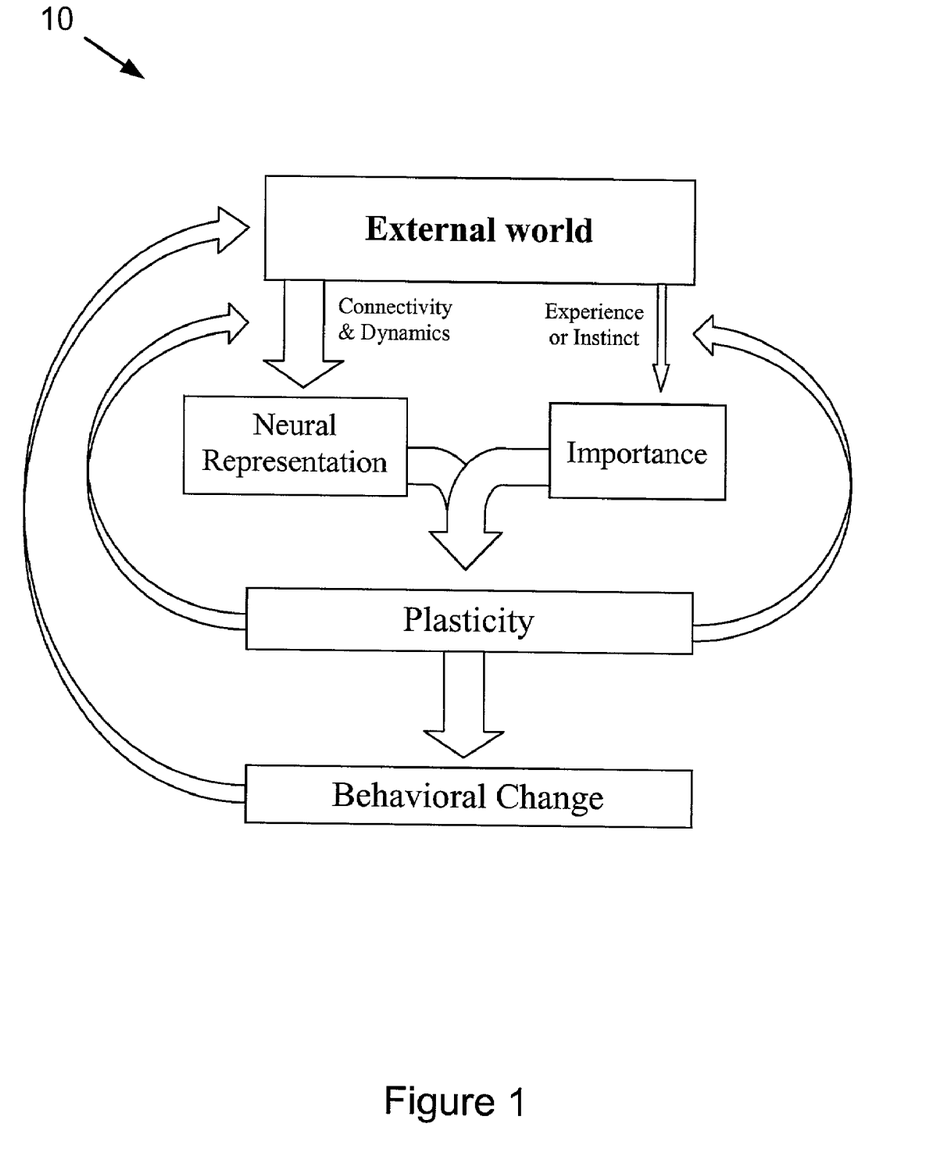
FIG. 1 summarizes a high level illustrative model of how feedback between perception, arousal, and behavior can contribute to either stability or instability learning mechanisms.

FIG. 1 summarizes a high level illustrative model 10 of how feedback between perception, arousal, and behavior can contribute to either stability or instability learning mechanisms, as described above and will be expanded upon below.

As the term is used herein, an abnormal behavior refers to any obsessive and other abnormal behaviorally self-sustaining sensations, perceptions and behaviors. This may include any one of the abnormal behaviors listed above or any abnormal behavior known to one of skill in the art. This may include for example, different classes of obsessions, traumatic stresses, persisting sensations, perseverative movements, and a wide variety of other over-learned behaviors. Obsessive or otherwise over-learned behaviors are manifested in a great variety of forms. For example, the present invention relates to computer-implemented methods for training people with obsessive compulsive behaviors, unsubstantiated fears, traumatic stress disorders, anxiety disorders or substance-related disorders. The techniques of the present invention may also be useful for a learning-based behavioral obsession, as well as for many related classes, in which progressive learning has deeply-embedded frequently reiterated and/or obsessive behaviors or ideations. For example, old and well-established habits may limit the ability of a person to acquire the listening and speaking skills to acquire a second language, or to develop a new manual skill. They may limit the ability of a person an individual to maintain their perceptual, cognitive and motor skills into old age. Unlearning of bad habits can greatly facilitate the learning of new, more useful habits.

2. Computer-Implemented Interaction

The present invention uses computer-implemented strategic and repetitive techniques of presenting computer-generated stimuli to a person that substantially alleviates an abnormal behavior over time. The computer-generated stimuli are contextually related to the abnormal behavior and may include visual, auditory and tactile information provided by the computer, or a peripheral device associated therewith. The stimuli may received by the person as sensory inputs, actions or events related to the abnormal behavior that may lead to actual activity, fear, obsession, or an associated trigger for the subject. In some cases, the stimuli may lead to obsessive fear, concern, pain, movement, or mental ideation related to the abnormal behavior.

In addition to the stimuli configured to trigger a response related to the abnormal behavior, the computer or its associated peripheral devices may present to the person a set of computer-implemented stimuli, tasks, and exercises that are configured to expedite neurochemical change in the subject, e.g., to induce dopamine production in the person. Stimuli provided by the computer is referred to as a task when the subject is required to execute a function in the computer interaction. Further, a task is referred to as a exercise when the subject's performance is monitored, either with or without the subject's awareness.

According to the present invention, weakening of the obsessive based neural representation may be achieved by individual targeted and computer-implemented stimuli, or by a varied program of stimuli that include both controlling the obsessive fear, concern, pain, movement, et alia, in appropriate timed relationship with exercises that promote dopamine release, in different behavioral exercises and contexts. In many cases, a more robust weakening of the neurological representation related to the obsessive behavior may be achieved by the richer contextual computer interaction provided by this more elaborate interaction strategy.

In other computer-implemented training exercises, obsessive inputs or actions are applied repetitively in non-attended, non-rewarded behavioral epochs in which the subject is required to attend to, respond to, and be rewarded by other parallel behaviors. This takes advantage of the second strategy for weakening the neurological expression of obsessive and over-learned behaviors.

The following discussion includes several exemplary computer-implemented interactive stimuli, tasks and exercises that may be presented to a subject for alleviating an abnormal behavior. It should be noted that the interactive computer-implemented apparatus, tests, tasks and exercises discussed below are exemplary, and given the interaction principles and directions discussed, numerous other interactive stimuli, tasks and exercises may be created and implemented for application with the present invention. One of skill in the art will appreciate the vast amount of stimuli that may be used for a particular abnormal behavior, and exhausted discussions thereof are omitted for sake of brevity.

Figure 2A:
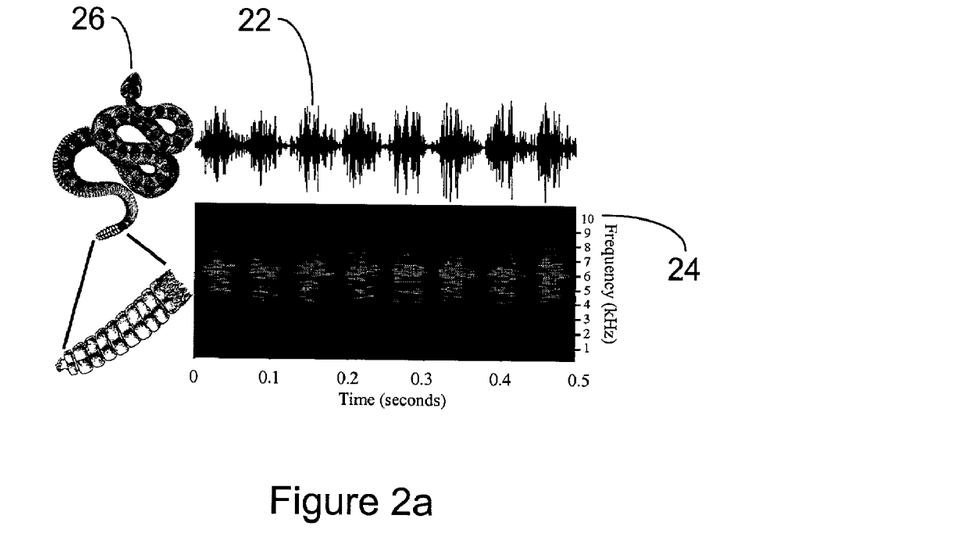
FIG. 2A illustrates the acoustic wave form and the spectrogram for the rattle of a western diamondback rattlesnake.

A person's fear of snakes will be used to illustrate a simple example of how the cortex learns to represent and adapt spatiotemporal patterns related to an abnormal behavior. FIG. 2A illustrates the acoustic wave form 22 and the spectrogram 24 for the rattle of a western diamondback rattlesnake 26. For purposes of discussion, it is assumed that either instinct or personal experience has provided the person a neural representation corresponding to wave form 22, with an impression that snakes can be dangerous, and with a phobia towards snakes in general.

Figure 2B:
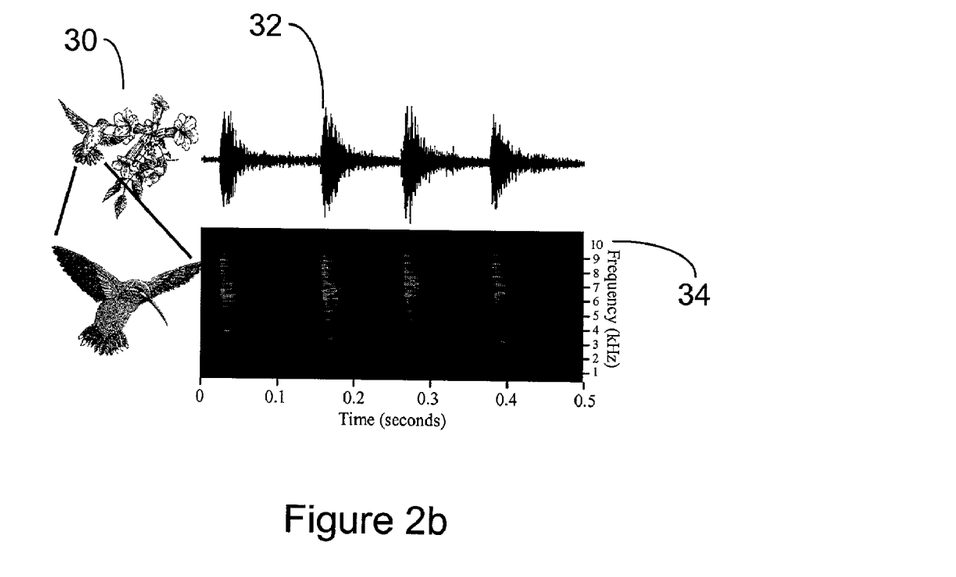
FIG. 2B illustrates the acoustic wave form and the spectrogram for the by the threats produced by the hummingbird.

Spectral analysis reveals that the snake's rattle is a rapidly modulated, narrow-band noise centered at six kHz (see spectrogram 24). The simplest way to avoid rattlesnakes is to associate the repeated activation of auditory neurons tuned to six kilohertz with danger. Unfortunately, even though the snake's rattle activates a limited region of the cortical frequency map, the population of engaged neurons is by no means unique to the snake's rattle. The same population of neurons is also activated of the much less dangerous rufous hummingbird 30, as shown in FIG. 2B. FIG. 2B also illustrates the acoustic wave form 32 and the spectrogram 34 for the by the threats produced by the hummingbird 30. The two sounds 22 and 32 have similar acoustic features, but indicate the presence of very different animals. These sounds 22 and 32 demonstrate the potential to confuse natural sounds. Confusion of these two warning sounds 22 and 32 could lead to either needless panic or a dangerous lack of caution for a person.

The computer-implemented techniques of the present invention are well suited to alleviate such a scenario. In accordance with one embodiment, computer generated acoustic stimuli is provided to a person that alters neural processing in order to "fine-tune" cortical coding to match the specific sensory output of rattlesnake 26. For example, computer-generated stimuli may continually promote the development of cortical neurons that reliably distinguish between rattlesnakes and hummingbirds by precisely adjusting the spectral and temporal filter properties of cortical neurons in the range of interest. As the cortical representation of the sounds is refined, the person would be better able to distinguish the two threats and would eventually recognize that the hummingbird vocalization does not indicate a snake is near. Alternatively, the computer-generated stimuli may be directed to improve the person's ability to detect the sound of rattlesnake 26 and not the hummingbird 30, and thereby correctly associate the sensory experience of rattlesnake 26 with danger and the hummingbird 30 as not dangerous.

As one of skill in the art will appreciate, there will be a large number of alternative sounds and inputs that the person may mistake as rattlesnake 26. The computer-implemented methods described herein may then be directed to a) differentiating each of these alternative inputs as not related to the phobia, or b) increasing the fidelity of the neural representation related to the phobia in a non-rewarded context.

Correspondingly, in one embodiment, the presentation of stimuli related to rattlesnake 26 is made in a non-attended context. As the term is used herein, a non-attended context refers to condition in which the subject's focus of attention is directed to another task or subject, with stimuli in the non-attended context that are outside of the active window or focus of attention, and may include states of awareness for the person associated with non-rewarding, non-learning, and non-behaving situations. In one embodiment, dopamine enticing computer-generated stimuli avoids the abnormal behavior related stimuli. It may be achieved, for example, by having a subject focus intensely on a specific, difficult behavioral task, while delivering other non-attended stimuli that are completely irrelevant to successful task performance. In this manner, briefly presented stimuli that would otherwise trigger an obsession or fear may have no effect when presented with an activity that requires intense concentration.

The presentation of stimuli to trigger the activity, fear, or obsession is typically progressive over time. In a specific embodiment to avoid strengthening of the stimuli, these abnormal behavior related stimuli will, initially, be only loosely related to the activity or obsession. As the computer-implemented interaction progresses and the obsessions or fears become less easily triggered, the stimuli may then become more closely linked to a powerful trigger. For acoustic stimuli contextually related to the phobia of snakes, this may include providing stimuli in a progression beginning with a band of noise including the specific sound frequency and temporal modulation of the snake, and progressively changing in a stepwise way so that the final stimuli closely simulate the noises generated by a warning snake.

Computer interaction to alleviate a person's snake phobia may also comprise visual stimuli related to the abnormal behavior. To further clarify how neural plasticity mechanisms that are normally adaptive can unbalance even a healthy brain, consider the challenge of visually discriminating rattlesnake 26 and a garden hose. Whether in a snake populated forest or the person's own backyard, the person must be able to detect snakes to avoid them. Detection is often complicated by the fact that snakes actively conceal themselves by hiding in shadows and tall grass. One way to improve the person's chances of detecting a hidden snake is to increase the proportion of visual cortex neurons that respond to curved or coiled objects (i.e. more visual "snake" neurons). It is believed that fear-induced activity, associated with each snake sighting, is sufficient to trigger the cortex to develop such responses.

Although more "snake-sensitive" neurons would increase the likelihood of detecting a concealed snake, they would also increase the chances of finding concealed sticks and garden hoses that resemble snakes. In the previous example, the two acoustic threats initially triggered the same fear response, but with computer interaction according to the present invention, the two became separable as the acoustic sensory representation was refined. This separability is possible because, although the two sounds are similar, there are reliable physical differences between them. When sensory information is ambiguous or noisy, learning is less precise and overgeneralization may result. As the visual system becomes more sensitive to snake-like objects, it will find more of them (especially in low contrast environments such as tall grass, dark alleys, and brush piles). As a result, learning mechanisms may be frequently paired with coiled garden hoses and curved sticks hidden in the grass and the representation of snake-like objects will be further expanded (FIG. 1). False alarms have the potential to trigger behavioral changes that may eventually contribute to the development of a full-blown phobia. The more time one spends scanning noisy, low-contrast areas looking for snakes, the more likely one is to find something that looks like a snake and to confirm the belief that snakes abound. A lowered threshold for detecting the shape of a snake coupled with active searching and fear can lead to excessive plasticity and instability.

This example illustrates that under certain circumstances the same mechanisms that regulate adaptive plasticity can lead to feedback interactions that destabilize the brain. Weakening of the snake phobia based neural representation may then be achieved by individual targeted and computer-implemented stimuli that are directed to improve the person's ability to differentiate visual stimuli that resembles the snake, and the snake itself. In this manner, the present invention may employ computer-implemented techniques and strategies for weakening the neurological representations of undesirable inputs, actions, ideations, or abnormal and obsessive behaviors.

In one embodiment, computer-implemented stimuli is delivered to a person in a timely manner to elicit dopamine release that reduces the neurological representation of an obsession or trigger. Dopamine is a valuable component in altering cortical representations. A cortical representation refers to the region of the cortex that responds to a specific stimulus (such as a sound of a given frequency or set of frequencies, and a given volume). The conditions for behaviorally generating the timed release of dopamine are well understood by one of skill in the art. Dopamine release can be enhanced through emotional events such as a reward. Often, dopamine is released as a direct function of the prediction of a behavioral reward. There are many forms of "rewards" that trigger its release. Repetitive rewards in a computer implemented setting can be i) material outside of information provided by the computer and related peripheral devices (food if you're hungry, water if you're thirsty, money if you value it, etc.), ii) information provided by the computer that holds an abstract value (e.g., "coins" or "points" that are "won" in a computer-implemented exercise or game that have some trade-in value), or iii) can relate to perceived success in goal achievement in a computer related exercise. In all of these and in many related instances, dopamine release contributes to the perception of satisfaction and pleasure associated with these rewards. In a specific embodiment, rewards are applied in what is called a "token economy", in which points are earned that are later substituted for money, prizes, or other rewards.

Thus, in one embodiment of the present invention, the individual is engaged in interactive computer-implemented exercises designed to alleviate an abnormal behavior. Preferably, the interactive exercises are designed to be sufficiently intensive, both in repetition and in the attentional focus related to the exercise difficulty, such that interspersed stimuli related to the abnormal behavior go unperceived. The exercises may also elicit dopamine production in a timely manner for the individual. In another embodiment, a computer-implemented exercise is provided to an individual with a learning-based behavioral obsession. In this exercise, the timed release of dopamine is controlled by delivering a reward or expectation of reward, followed by the systematic delivery of images, sounds or other dimensions, or of stimulus events or the evocation of actions that predictably trigger the abnormal behavior.

In another embodiment, instead of releasing dopamine by controlling its release in behavior using computer-generated stimuli, dopamine may be released in a non-behaving person by electrically stimulating one or more brain centers (such as the "ventral tegmental it area") that provide dopamine to the cerebral cortex. Again, the release is performed in a timely manner relative the presentation of stimuli that is to be unlearned.

For example, the behavioral obsession may be an obsessive compulsive need to wash one's hands. In this case, the computer-generated stimuli corresponding to images that may trigger the person to wash their hands may include images such as dirt, doorknobs, handshaking, picking up a pencil, the color brown, etc. The preceding list of potentially disturbing visual stimuli are provided in descending order of severity for the hand-washing obsession (although the list may vary from person to person). As computer-implemented interaction of the present invention proceeds, and stimuli of decreased severity are progressively overcome in terms of eliciting an undesirable response from the person, stimuli of increased severity may then be presented to further facilitate alleviating the obsessive abnormality. In this manner, the obsessive person learns to separate real dangers from input mistaken or learned as a threat. To facilitate this learning process, the timed release of dopamine is controlled by delivering a reward or expectation of reward in a computer-implemented game or exercise, followed by the systematic delivery of computer-generated images, such as those provided above, that predictably trigger the abnormal behavior.

3. Feedback & Assessment

Some brain and body assessment measures might alter when the person reacted to stimuli related to the abnormal behavior. This reaction to abnormal behavior related stimuli may be used as feedback in assessment. In one embodiment, peripheral computer devices associated with the person interacting with the computer receive input from the person that indicates whether and when the person saw or heard stimuli that lead to a trigger. For example, a galvanic skin response may be used to detect whether and when the person reacts to stimuli related to the abnormal behavior. The galvanic skin response includes changes in skin conductance resulting from sweat production produced when a person consciously or unconsciously reacts. As one of skill in the art will appreciate, such a response is easily detectable by a computer peripheral device associated with a computer. The device may provide binary feedback to the response (did they respond?), or more complex feedback including temporal and quantitative information describing the person's response to a specific stimulus. Other brain and body measures detectable by a computer peripheral may include blood pressure, temperature, and heart rate, for example. Since these measures indicate a person's response to a trigger related to the abnormal behavior, the computer-implemented apparatus used herein may include one or more sensors for detecting such a measure.

The feedback may be useful for a number of reasons. Firstly, the assessment measures may be used to determine the computer-interaction duration (e.g., knowing when to stop), frequency, and type of stimuli used (e.g., knowing when to change to less distant stimuli). Alternatively, the assessment measures are applicable before a computer-implemented interaction program to get a pre-interaction indication of the individual's capacities and after interaction to facilitate comparison.

From the early discussion provided herein, it is evident that the building and deterioration of an abnormal behavior in the brain is progressive. Correspondingly, there exists a continuum of abnormal behavior presence from minimally present to severe levels which the computer-implemented methods of the present invention may be used in an assessment strategy to detect and build a representation thereof. Thus, in one embodiment of the present invention, the computer-implemented interaction techniques are used to assess the level of progression of the abnormal behavior for a human subject. This assessment strategy may then be used to facilitate alleviating the abnormal behavior for a person as described above.

Computer-implemented feedback may also allow improved diagnosis and assessment of the abnormal behavior. As the computer-implemented tests may obtain immediate, automated, and quantitative computer-based feedback, assessment may then be provided at levels greater than traditional clinical methods relying on interpersonal awareness. Indeed, the automated feedback may advantageously enable a meter of behavior progression and a monitoring tool for interaction efficacy—even when the person is not conscious of a trigger to a particular stimulus. This is in contrast to conventional methods which are typically limited to a qualitative assessment based on self or clinical perception. As the presence of the abnormal behavior is conventionally initially detected after some undesirable and physically or socially detectable manifestation, it is most common that the neurological representation underlying the abnormal behavior has progressed considerably before personal or clinical perception to include numerous stimuli that the person is not aware of. Computer-based assessment according to the present invention may then improve diagnosis and assessment of the abnormal behavior relative to these perception based models.

The computer-implemented methods may also advantageously permit quantitative assessment of an individual's reactions. By way of example, the computer-implemented assessment may include a temporal reconstruction of physical feedback (such as a galvanic skin response) which provides a quantitative dynamic reaction of the person to one or more triggers. For example, the quantitative assessment may involve measuring the temporal galvanic skin response to various trigger stimuli to assess the severity of each stimuli for an individual. This quantitative dynamic response may then be used as a quantitative basis for continuing assessment. Physical responses reflected by changes in the iris, or signaled for example by small physical movements of the eyes, body or hands can be detected, and used to determine the effectiveness of the alleviation of the obsession or bad habit after each presentation of these training stimuli. Obsessions also generate abnormal brain responses whose magnitudes can reflect the power of the obsession. Measurement of these responses can be used to objectively assess the alleviation of the obsession. Further, a representation of behavior progression for an individual may be constructed from numerous interactive sessions to quantitatively map efficacy of the computer implemented interaction and/or progression of the behavior over time.

In yet another embodiment, the computer-implemented assessment techniques may also be used to define and test individuals considered to be at high risk of displaying the abnormal behavior. Again the goal may be to detect the presence of the abnormal behavior earlier than conventional methods, thus enabling earlier treatment. In one embodiment, a predictive method is used before onset of perceived symptoms and behaviors. This predictive method may enhance the conventional strategies used by clinicians in an automated and more accurate manner. For example, the assessment may involve measuring the response to various stimuli related to the abnormal behavior to assess the whether the person reacts to each stimuli.

In addition to the computer-implemented methods implemented before treatment, the assessment may be included regularly in the computer-implemented interaction described above, e.g., on a daily basis or periodically during interaction. Alternately, the assessment may be implemented after significant treatment as a predictive measure to determine if the individual may regress.

4. Exemplary Continued Computer-Implemented Interaction

Figure 3:
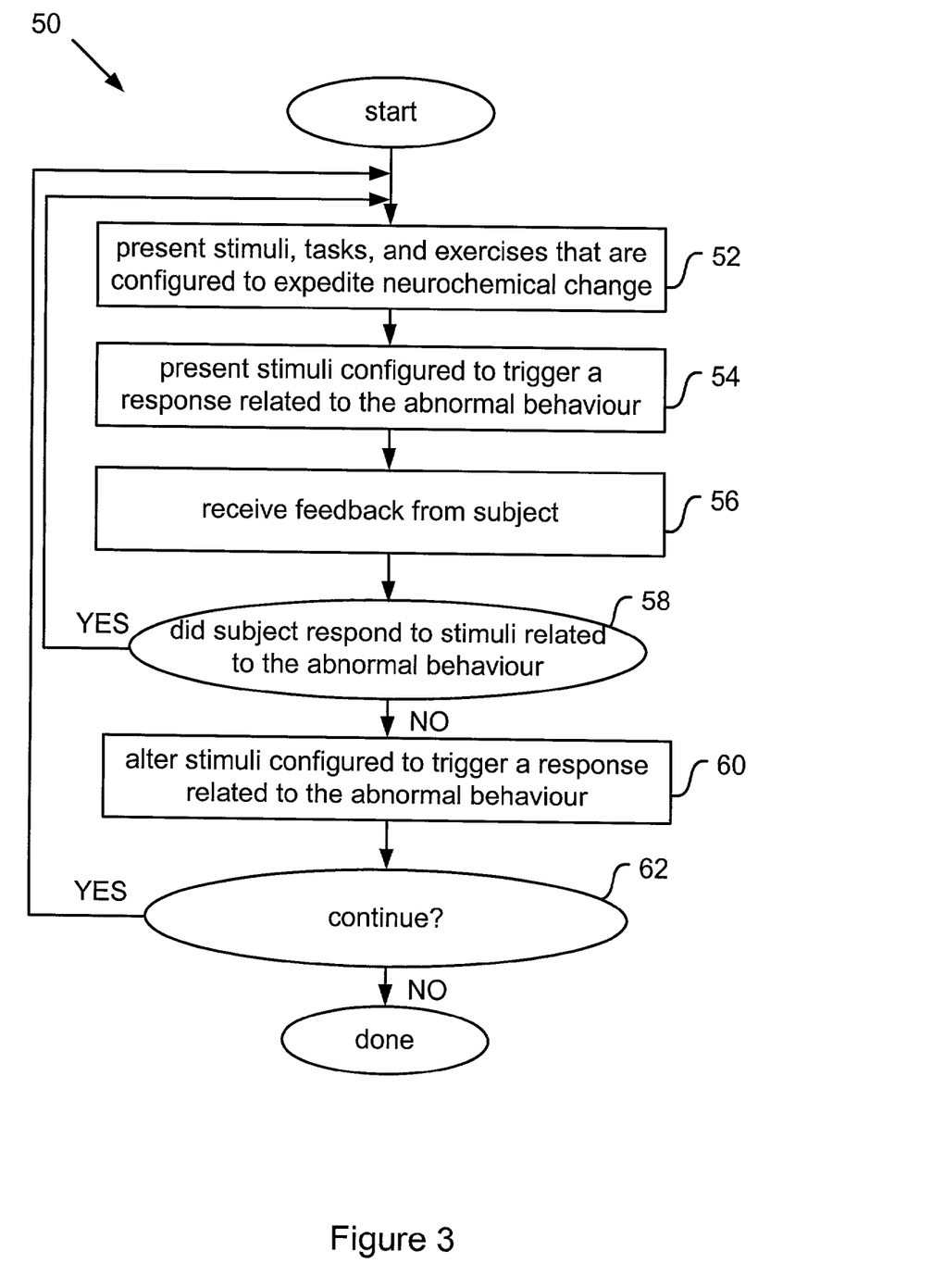
FIG. 3 illustrates a process flow for alleviating an abnormal behavior in accordance with one embodiment of the present invention.
Figure 4A:
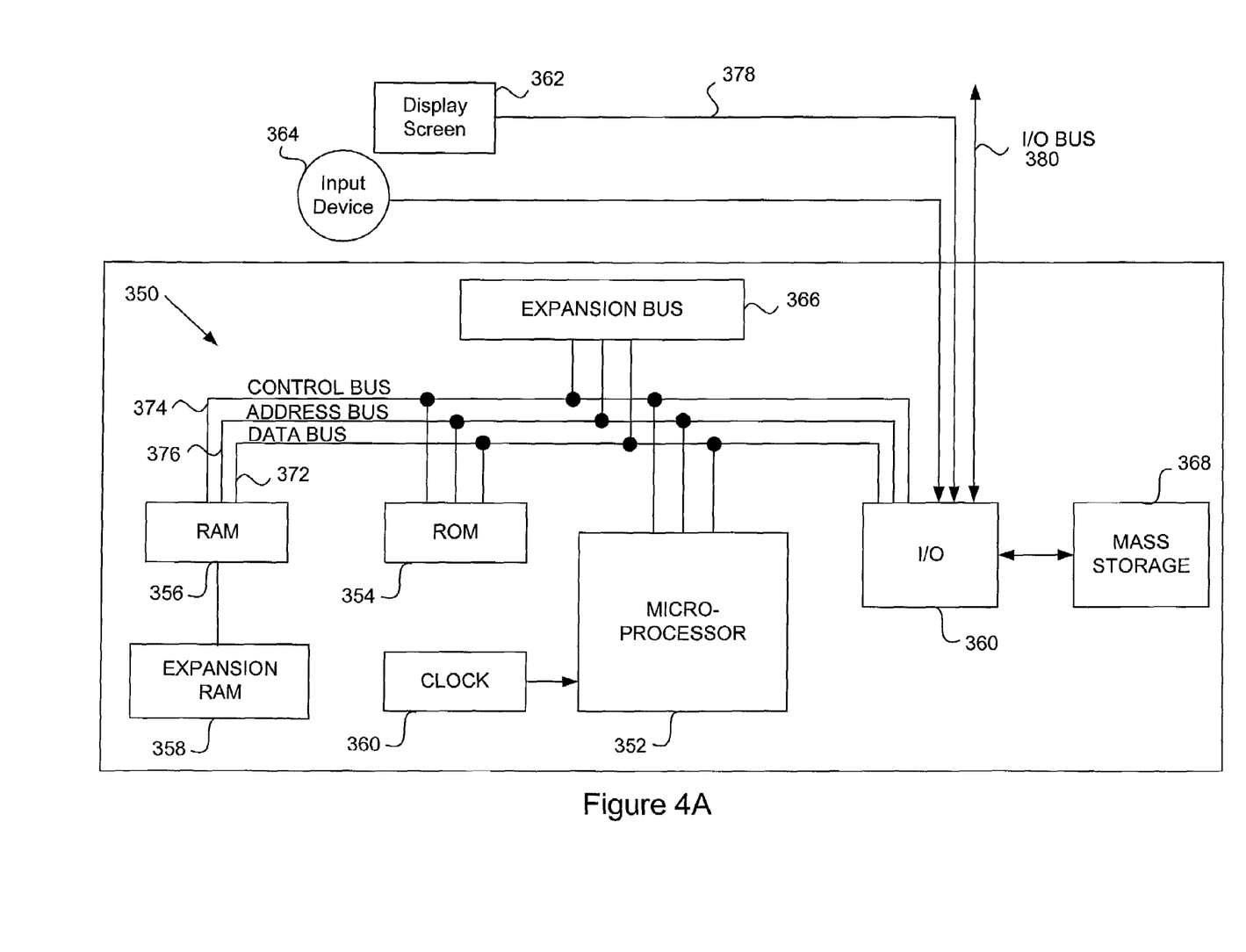
FIG. 4A illustrates an exemplary general-purpose computer system, representing a computer suitable for implementing the present invention.

FIG. 3 illustrates a process flow 50 for alleviating an abnormal behavior in accordance with one embodiment of the present invention. Process flow 50 may employ any computer-based apparatus, such as the apparatus described with respect to FIG. 4. Processes in accordance with the present invention may include up to several additional steps not described or illustrated here in order not to obscure the present invention. While alleviating an abnormal behavior will now be described as a method, those skilled in the art will recognize that the present invention encompasses a system or software having units capable of performing the actions as described below.

Process flow 50 begins by presenting to the subject, using the computer-based apparatus, one of a set of computer-implemented stimuli, tasks, and exercises that are configured to expedite neurochemical change in the subject (52). In one embodiment, the set of computer-implemented stimuli, tasks, and exercises that are configured to increase expression of dopamine in the subject. In this case, the stimuli, tasks, and exercises may be selected for their ability to engage the patient's intense, trial-by-trial attentional focus while at the same time ensuring that the patients are substantially rewarded. For example, a computer-implemented exercise may be a game (e.g., tetris) that demands execution of a cognitive skill (e.g., spatial planning). In this case, a reward may be provided for a correct and near correct performance in the game, or reaching a particular score. To maintain the aforementioned intensity, the stimulus sets and exercise challenge may be adjusted over time to maintain novelty or difficulty in light of the subject's changing ability or attentional level. Additionally, the computer-implemented mechanisms may implement various computer graphics and animations to facilitate a high level of engagement by the individual.

Subsequently, the computer-implemented stimuli configured to trigger a response related to the abnormal behavior are presenting to the subject (54). In one embodiment, the stimuli related to the abnormal behavior (54) are presented in a random, non-rewarded context while the person attends to other stimuli (52) and performs other actions that require a high level of engagement and attention. In a specific embodiment, the person's actions in response to the computer-implemented stimuli (52) are a behavioral interaction task. This provides a second computer-implemented strategy for weakening the representations of an abnormal behavior or obsession. This second computer-implemented strategy may be embodied in many possible forms and applied to various individuals, such as those with different classes of obsessions, traumatic stresses, persisting sensations, perseverative movements, and a wide variety of other overlearned behaviors.

As mentioned before, dopamine release weakens the representations of inputs or actions or obsessions if it is released shortly before that input or action or obsessive reiteration. In one embodiment, the stimuli, tasks, and exercises that are presented to increase expression of dopamine in the subject are presented before the stimuli configured to trigger a response related to the abnormal behavior. In a specific embodiment, a stimuli, task, or exercise used to elicit dopamine production is presented in the range of about 10 milliseconds to about 2 seconds before the stimuli including context related to the abnormal behavior. In some cases, the stimuli, task, or exercise is presented in the range of about 0 milliseconds to about 60 seconds or even longer before the behavior related stimuli. Feedback may then be received from the subject that indicates whether the stimuli including context related to the abnormal behavior triggered a response (56). In order to monitor or improve progression of the interaction, the salience of the obsession, activity, or fear could be assessed periodically, or every session, using one or more of the sensing mechanisms as described above.

If a response was detected, than the stimuli may be presented again, either using different conditions, or under similar conditions—or different stimuli may be used—until the subject does not react. This repetition may proceed until the subject doesn't react a number of times to the stimulus to further strengthen the neurological changes. At this point, the stimuli configured to trigger a response in the subject is altered in a manner that progressively works towards alleviating the abnormal behavior. As mentioned before, this may include altering the context of the stimuli to a less distant trigger, or altering the stimuli itself. Altering the context of the stimuli may include, for example, using visual or auditory stimuli that more closely resembles a phobia, such as using a plane image instead of a bird image for visual stimuli for a person with a flying phobia. Altering the stimuli itself may include manipulating the visual presentation of the stimuli by increasing its size, colors, or other particular details associated with the stimulus.

If desired, the above process is continued (62). In one embodiment to inure patients to an obsession and thereby weaken response to stimuli related to the obsession, the computer-implemented techniques provide computer-implemented interaction on a heavy, repetitive schedule. In a specific embodiment, the set of computer-implemented stimuli, tasks, and exercises that are configured to increase expression of dopamine in the subject (52), and the computer-implemented stimuli including context related to the abnormal behavior (54), are administered a high number of times per day. By way of example, hundreds of stimuli and exercises per day may be administered to the subject to ensure that the neurochemical change mechanisms are sufficiently stimulated. It is contemplated that computer interaction may last at least thirty minutes per day and may extend to as many hours as necessary, limited only by the subject's interest level, stamina, and attentional focus. The exact number of stimuli and exercises depends on many factors, including the length of each exercise, the attentional focus required, the mental endurance of the subject, and the like. In a specific embodiment, computer sessions are provided for 1–2 hours per day for 5 days/week over a 2–4 week period. In some cases, it is preferable, although not necessary, that interaction be performed every day to ensure continued progress. In a single day, stimuli related to the abnormal behavior may be administered in the range of about 100 and about 2,000 times, for example. In some cases, stimuli including context related to the abnormal behavior may be administered for about 1 to about 100 days. Irrespective of the exact format and duration of interaction, the intensive interactive computer-implemented interaction is configured to be sufficiently intensive to fundamentally change the neurochemical representation believed to underlie the abnormal behavior and any of its related behavioral effects.

The computer interaction will typically comprise strategically and repeatedly presenting the stimuli (52). At a minimum, the computer-implemented interaction aims to significantly reduce undesirable, personally noticeable or otherwise, effects associated with the abnormal behavior. Preferably, the computer interaction focuses on alleviating a behaviorally abnormal self-sustaining behavior by unlearning the behavior. The interaction may further extend to continuously re-enforcing the unlearning over time. For example, the interaction may proceed as long as the person lives, or some shorter suitable time. In some cases, the computer-implemented interaction proceeds past the perceptual disappearance of the abnormal behavior. As the atmosphere associated with the learning the abnormal behavior may be in effect after interaction finishes, the interaction may continue prophylactically. In other words, the computer-implemented interaction may proceed for an extended period of time, or as long as necessary, to alleviate a potential return of the abnormal behavior. For example, interaction may continue periodically for a month or two after clinical or self-perceptual disappearance of the abnormal behavior.

In accordance with one aspect of the present invention, there are provided methods and apparatus for remote computer-implemented interaction directed to alleviate an abnormal behavior. By remote (i.e., local to the human subject) interaction on a frequent basis, the practical inconveniences and potential inaccuracies of prior art therapy techniques are advantageously avoided. Due to the convenience of the remote computer-implemented interaction techniques, it may be possible to administer the stimuli and exercises in less time than it would take to travel to a therapy center. In addition, the remote computer-implemented interaction on a high frequency basis may allow for improved interaction by screening out random variation such as varying test times, travel factors such as fatigue, or mental factors involved in testing a person in an unfamiliar setting such as a hospital or an office.

In another embodiment, the present inventive techniques may be employed as an adjunct to conventional approaches to treating an abnormal behavior. That is, progress provided by the interactive computer-implemented methods described herein may reduce or eliminate the dosage of a biochemical therapy containing used in treating the abnormal behavior parallel to the computer-implemented methods described herein.

5. Exemplary Computer-Based Apparatus

The computer-implemented techniques of the present invention will typically be based on a number of computer-generated stimuli provided by a suitable computer-based apparatus.

Referring to FIG. 4A, an exemplary computer system 350 includes a central processing unit (CPU) 352, read only memory (ROM) 354, random access memory (RAM) 356, expansion RAM 358, input/output (I/O) circuitry 360, display assembly 362, input device 364, and expansion bus 366. Computer system 350 may also optionally include a mass storage unit 368 such as a disk drive unit or nonvolatile memory such as flash memory and a real-time clock 360. In one embodiment, mass storage unit 368 may include units which utilizes removable computer readable media, such as floppy disks, opto-magnetic media, optical media, and the like for the storage of programs and data.

CPU 352 is preferably a commercially available, single chip microprocessor such as one of the Intel X86 (including Pentium™) or Motorola 680XX family of chips, a reduced instruction set computer (RISC) chip such as the PowerPC™ microprocessor available from Motorola, Inc, or any other suitable processor. CPU 352 is coupled to ROM 354 by a data bus 372, control bus 374, and address bus 376. ROM 354 may partially contain the basic operating system for the computer system 350. CPU 352 is also connected to RAM 356 by busses 372, 374, and 376 to permit the use of RAM 356 as scratch pad memory. Expansion RAM 358 is optionally coupled to RAM 356 for use by CPU 352. CPU 352 is also coupled to the I/O circuitry 360 by data bus 372, control bus 374, and address bus 376 to permit data transfers with peripheral devices.

I/O circuitry 360 typically includes a number of latches, registers and direct memory access (DMA) controllers. The purpose of I/O circuitry 360 is to provide an interface between CPU 352 and such peripheral devices as display assembly 362, input device 364, mass storage 368, and/or any other I/O devices. I/O circuitry 360 may also include analogto-digital (A/D) converters, digital-to-analog (D/A) converters, as well as other control circuits for controlling and receiving feedback data from the I/O devices. The I/O devices suitable for generating stimuli to be administered to the subject and for receiving responses therefrom may be coupled to I/O bus 380 of computer 350. They are discussed in greater detail with reference to FIG. 4B. Display assembly 362 of computer system 350 is an output device for displaying objects and other visual representations of data, and presenting visual stimuli.

The screen for display assembly 362 can be a device that uses a cathode-ray tube (CRT), liquid crystal display (LCD), or the like, of the types commercially available from a variety of manufacturers. Input device 364 can be a keyboard, a mouse, a stylus working in cooperation with a position-sensing display, or the like. Alternatively, input device 364 can be an embedded RF digitizer activated by an "active" RF stylus. As a further alternative, input device 364 may be any type of switch capable of communicating a test subject's response to computer system 350. Therefore, as used herein, the term input device will refer to any mechanism or device for entering data and/or pointing to a particular location on a screen of a computer display. One or more input devices may be provided to control computer 350 and/or to receive responses from the test subject. The aforementioned input devices are available from a variety of vendors and are well known in the art.

Some type of mass storage 368 is generally considered desirable. However, mass storage 368 can be eliminated by providing a sufficient amount of RAM 356 and expansion RAM 358 to store user application programs and data. In that case, RAMs 356 and 358 can optionally be provided with a backup battery to prevent the loss of data even when computer system 350 is turned off. However, it is generally desirable to have some type of long term mass storage 368 such as a commercially available hard disk drive, nonvolatile memory such as flash memory, battery backed RAM, PC-data cards, or the like.

Figure 4B:
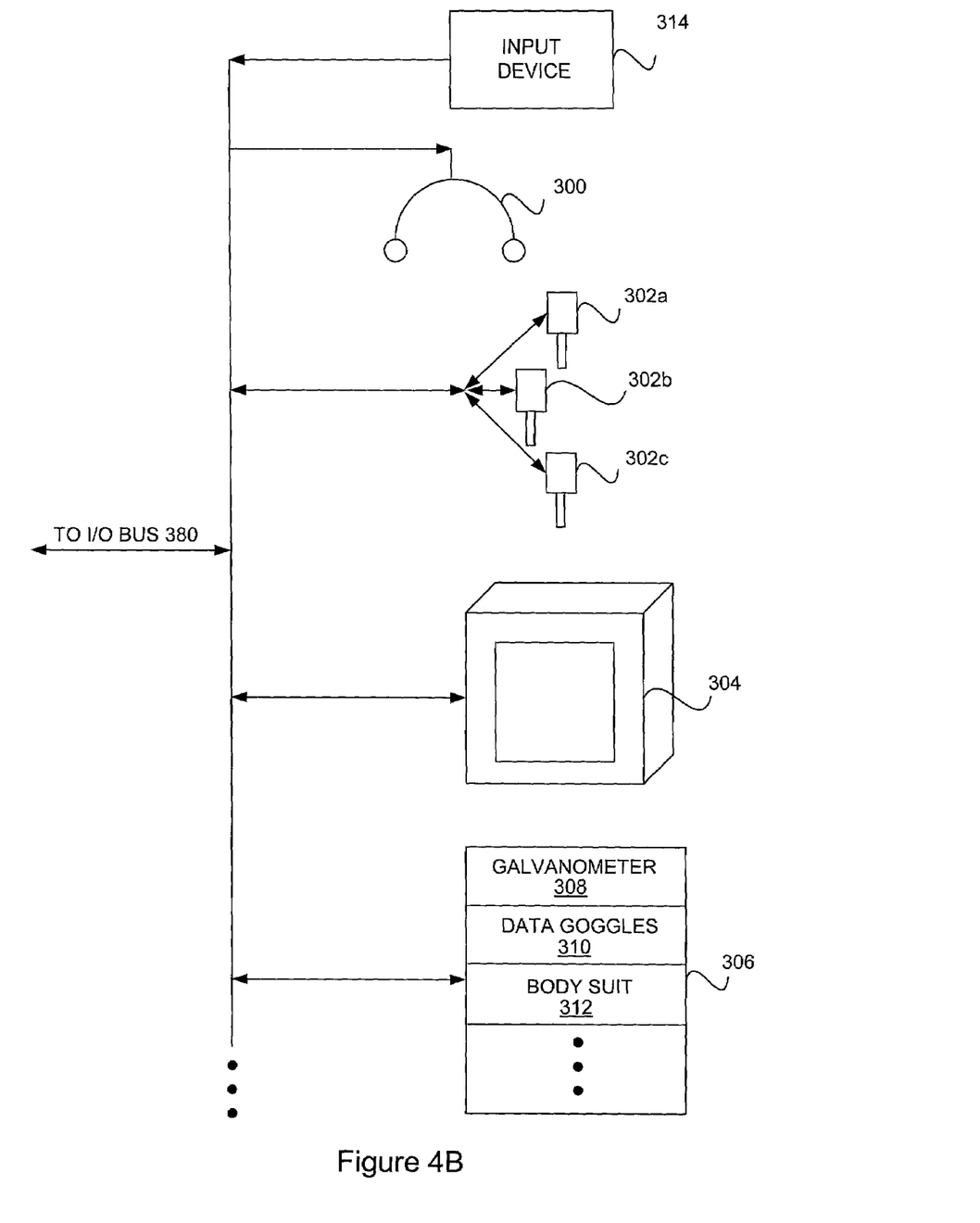
FIG. 4B illustrates some exemplary peripheral devices used in association with the general purpose computer system of FIG. 4A.

In FIG. 4B, some exemplary peripheral devices are shown, including headphone 300 (for delivering auditory stimuli), computer-controlled probe 302 (for delivering touch stimuli), visual stimuli generator 304 (for delivering visual stimuli), and/or virtual reality apparatus 306 (for delivering stimuli to and receiving responses from the test subject in a virtual manner through any of the senses). In general, these I/O devices may interface with computer system 350 via I/O circuit 360 or an appropriate interface circuit, which may be external to computer 350 and/or dedicated to the I/O device. Visual stimuli generator 304 may represent, for example, any light generating device such as a light bulb, a flash device, another computer display screen or the like if such is employed instead of display screen 362 of computer 350 for providing visual stimuli to the test subject. Virtual reality apparatus 306 may include, for example galvanometer 308, virtual goggles 310, body suit 312, or the like, some of which may be able to both deliver the stimuli to the test subject as well as sense the responses therefrom. An optional input device 314 is also shown, representing a dedicated input device, such as a switch, for receiving responses from the test subject. Optional input device 314 is provided when it is desired to receive responses to the test stimuli from the test subject through an input device other than input device 364 of computer 350.

In operation, computer system 350 is employed to generate control signals to the stimuli generator(s) to produce the stimuli of the various tests. These stimuli are then furnished to the test subject for assessment and/or training, and the responses from the test subject may then be recorded by input device 364 and/or input device 314 and analyzed by CPU 352. If desired, feedback to the test subject may be given at various stages of the test(s) via, for example, display assembly 362.

It should be borne in mind that although computer system 350 is discussed in some detail herein to facilitate discussion, the invention may be practiced using a variety of suitable computer-implemented techniques. In general, any suitable computer system may be employed for generating control signals to the stimuli generators and receive feedback from the input device(s). Further, the inventive computer interaction techniques disclosed herein may be implemented via a computer network, such as a local area network (LAN), wide area network (WAN) or a global computer network such as the Internet. In the latter cases, the inventive computer-implemented interaction techniques may be implemented at least in part as downloadable computer software and data (e.g., applets such as JAVA™ applets from Sun Microsystems Inc.). The downloadable computer software and data may be kept on one or more servers on the network, accessible by any client computer or terminal capable and authorized for such access. The client computer/terminal may then be employed to control an appropriate stimuli generator and to gather responses from the test subject. To facilitate interaction, the downloadable computer software and data can be downloaded once and reused over and over at the client computer/terminal. Alternatively, the downloadable computer software and data can be downloaded for each individual interaction session via the network as needed. In some cases, the computer software may be executed at the servers themselves, with program outputs transmitted to the client computer/terminal for interfacing with the I/O devices. Network computing techniques and implementations therefor are well known in the art and are not discussed in great detail here for brevity's sake.

While this invention has been described in terms of several preferred embodiments, there are alterations, permutations, and equivalents which fall within the scope of this invention which have been omitted for brevity's sake. It is therefore intended that the scope of the invention should be determined with reference to the appended claims.

What is claimed is:

1. A computer-implemented method for alleviating an abnormal behavior for a human subject, the computer-implemented method employing a computer-based apparatus associated with one or more peripheral devices, the computer-implemented method comprising:
    presenting to the subject, using the computer-based apparatus, one of a set of computer-implemented stimuli, tasks, and exercises that are exercises that are configured to expedite neurochemical change in the subject wherein the exercises are configured to increase expression of dopamine in the subject;
    presenting, using the computer-based apparatus, a computer-implemented stimuli including context related to the abnormal behavior,
    wherein the one of the set of computer-implemented stimuli, tasks, and exercises is presented in the range of about 10 milliseconds to about 2000 milliseconds before the stimuli including context related to the abnormal behavior is presented; and
    altering, using the computer-based apparatus, the computer-implemented stimuli including context related to the abnormal behavior, wherein the altering of the stimuli including context facilitates alleviating the abnormal behavior.

2. The computer-implemented method of claim 1 wherein the one of the set of computer-implemented stimuli, tasks, and exercises is presented in the range of about 0 milliseconds to about 60 seconds before stimuli including more complex contests related to the abnormal behavior is presented.

3. The computer-implemented method of claim 1 wherein the set of computer-implemented stimuli, tasks, and exercises is directed to elicit a high level of engagement from the human subject.

4. The computer-implemented method of claim 1 wherein the set of computer-implemented stimuli, tasks, and exercises are rewarding to the subject.

5. The computer-implemented method of claim 4 wherein the set of computer-implemented stimuli, tasks, and exercises comprise information provided by the computer that holds an abstract value.

6. The computer-implemented meted of claim 1 wherein the altering is directed to vary the subject's ability to trigger an episode related to the abnormal behavior.

7. The computer-implemented method of claim 6 wherein the altering comprises providing a new stimulus that is more likely to trigger an episode related to the abnormal behavior for the subject.

8. The computer-implemented method of claim 1 wherein the visual or auditory stimuli includes visual or auditory information provided by a peripheral in association with the computer-based apparatus.

9. The computer-implemented method of claim 1 wherein the presenting and altering is repeatedly administered a number of times effective to alleviate the abnormal behavior.

10. The computer-implemented method of claim 9 wherein the stimuli including context related to the abnormal behavior is administered between about 100 and about 2,000 times per day.

11. The computer-implemented method of claim 9 wherein the stimuli including context related to the abnormal behavior is administered for about 1 to about 100 days.

12. The computer-implemented method of claim 1 wherein the computer-implemented method is provided by a remote computer local to the subject.

13. The computer-implemented method of claim 1 wherein the stimuli including context related to the abnormal behavior is presented in a manner that is non-attended by the subject.

14. The computer-implemented method of claim 1 wherein the method is employed as an adjunct to a conventional approach to treating an abnormal behavior.

15. The computer-implemented method of claim 1 wherein the stimuli including context related to the abnormal behavior are configured to trigger a response in the subject.

16. The computer-implemented method of claim 19 further comprising obtaining feedback from the subject that indicates whether the subject reacted to the stimuli including context related to the abnormal behavior.

17. The computer-implemented method of claim 15 further comprising building a representation of behavior progression for the subject.

18. A computer-implemented method for assessing an abnormal behavior for a human subject, the computer-implemented method employing a computer-based apparatus associated with one or more peripheral devices, the computer-implemented method comprising:
    presenting, using the computer-based apparatus, a computer-implemented stimuli including context related to the abnormal behavior; and
    obtaining, using the computer-based apparatus, feedback from the subject that indicates whether the subject reacted to the stimuli including context related to the abnormal behavior,
    wherein the feedback provides information corresponding to a quantitative dynamic reaction of the person to a trigger in the stimuli.

19. The computer-implemented method of claim 18 further comprising building a representation of behavior progression for the subject.

20. A computer readable medium including instructions for alleviating an abnormal behavior for a human subject the instructions employing a computer-based apparatus associated with one or more peripheral devices, the instructions comprising:
    instructions for presenting to the subject, using the computer-based apparatus, one of a set of computer-implemented stimuli tasks, and exercises that are configured to expedite neurochemical change in the subject wherein the exercises are configured to increase expression of dopamine in the subject;
    instructions for presenting, using the computer-based apparatus, a computer-implemented stimuli including context related to the abnormal behavior, wherein the one of the set of computer-implemented stimuli, tasks, and exercises is presented in the range of about 10 milliseconds to about 2000 milliseconds before the stimuli including context related to the abnormal behavior is presented; and instructions for altering, using the computer-based apparatus, the computer-implemented stimuli including context related to the abnormal behavior, wherein the altering of the stimuli including context facilitates alleviating the abnormal behavior.

21. A computer-implemented method for delivering computer readable instructions for alleviating an abnormal behavior for a human subject, the instructions employing a computer-based apparatus associated with one or more peripheral devices, the method comprising:

transmitting, over a signal transmission medium, signals representative of instructions for presenting to the subject using the computer-based apparatus, one of a set of computer-implemented stimuli, tasks, and exercises that are configured to expedite neurochemical change in the subject wherein the exercises are configured to increase expression of dopamine in the subject;

transmitting, over a signal transmission medium, signals representative of instructions for presenting, using the computer-based apparatus, computer-implemented stimuli including context related to the abnormal behavior, wherein the one of the set of computer-implemented stimuli, tasks, and exercises is presented in the range of about 10 milliseconds to about 2000 milliseconds before the stimuli including context related to the abnormal behavior is presented; and transmitting, over a signal transmission medium, signals representative of instructions for altering, using the computer-based apparatus, the computer-implemented stimuli including context related to the abnormal behavior, wherein the altering of the stimuli including context facilitates alleviating the abnormal behavior.

* * * * *